United States Patent [19]

Schnabel et al.

[11] Patent Number: 5,696,053

[45] Date of Patent: Dec. 9, 1997

[54] NITROGEN-SUBSTITUTED PHENYLSULFONYLUREAS; PROCESSES FOR THEIR PREPARATION, AND THEIR USE AS HERBICIDES AND PLANT GROWTH REGULATORS

[75] Inventors: Gerhard Schnabel, Grosswallstadt; Lothar Willms, Hofheim; Klaus Bauer, Hanau; Hermann Bieringer, Eppstein, all of Germany

[73] Assignee: Hoechst Aktiengesellschaft, Frankfurt, Germany

[21] Appl. No.: 453,967

[22] Filed: May 30, 1995

[30] Foreign Application Priority Data

Jun. 1, 1994 [DE] Germany .................. 44 19 259.2

[51] Int. Cl.$^6$ .................. C07D 239/69; A01N 43/54
[52] U.S. Cl. .................. 504/214; 504/215; 544/321; 544/331; 544/332; 544/327; 540/481; 540/601
[58] Field of Search .................. 504/214, 215; 544/321, 331, 332, 327; 540/481, 601

[56] References Cited

U.S. PATENT DOCUMENTS

| | | | |
|---|---|---|---|
| 4,632,695 | 12/1986 | Schurter et al. | 544/211 |
| 4,664,695 | 5/1987 | Schurter et al. | 544/321 |
| 4,892,946 | 1/1990 | Levitt | 544/321 |
| 4,981,509 | 1/1991 | Hillemann | 544/211 |
| 5,157,119 | 10/1992 | Compopiano et al. | 544/211 |

FOREIGN PATENT DOCUMENTS

| | | |
|---|---|---|
| 0001515 | 4/1979 | European Pat. Off. . |
| 0116518 | 8/1984 | European Pat. Off. . |
| 0304282 | 2/1989 | European Pat. Off. . |
| 42 36 902 | 8/1994 | Germany . |

Primary Examiner—John M. Ford
Attorney, Agent, or Firm—Curtis, Morris & Safford, P.C.

[57] ABSTRACT

Salts of the formula (I)

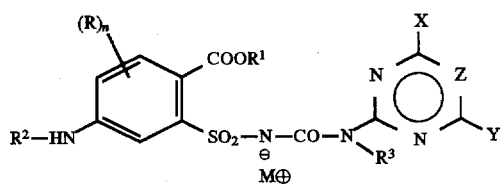

in which n is 0, 1, 2 or 3,

R is halogen, alkyl or alkoxy, mainly in each case independently of other substituents R in the event that n is greater than 1, $R^1$ is a substituted or unsubstituted hydrocarbon radical or a substituted or unsubstituted heterocyclic radical, $R^2$ is an acyl radical, $R^3$ is hydrogen or $C_1$–$C_5$-alkyl, M⊕ is a metal or ammonium ion, X and Y independently of one another are halogen, $C_1$–$C_6$-alkyl, $C_1$–$C_6$-alkoxy or $C_1$–$C_6$-alkylthio, each of the three last-mentioned radicals being unsubstituted or substituted by one or more radicals selected from the group consisting of halogen, $C_1$–$C_4$-alkoxy and $C_1$–$C_4$-alkylthio, or are $C_3$–$C_6$-cycloalkyl, $C_2$–$C_6$-alkenyl, $C_2$–$C_6$-alkynyl, $C_3$–$C_6$-alkenyloxy, $C_2$–$C_6$-alkynyloxy, mono- or di($C_1$–$C_4$-alkyl)amino, and Z is CH or N, are suitable as herbicides and plant growth regulators, The compounds (I) can be prepared by processes of claims 5 to 7, for example by hydrogenating 2-alkoxycarbonyl-5-nitrophenylsulfonylureas in the presence of anhydrides.

10 Claims, No Drawings

NITROGEN-SUBSTITUTED PHENYLSULFONYLUREAS; PROCESSES FOR THEIR PREPARATION, AND THEIR USE AS HERBICIDES AND PLANT GROWTH REGULATORS

The invention is in the technical field of herbicides and plant growth regulators, in particular of herbicides for the selective control of broad-leaved weeds and grass weeds in crops of useful plants.

It has been disclosed that heterocyclically substituted phenylsulfonylureas which have an amino group or functionalized amino group attached to the phenyl ring have herbicidal and plant growth-regulating properties; see EP-A-1515, U.S. Pat. No. 4,892,946, U.S. Pat. No. 4,981,509, EP-A-116 518 (=U.S. Pat. No. 4,664,695, U.S. Pat. No. 4,632,695), DE-A-4236902 (WO 94/10154).

Surprisingly, it has now been found that salts of certain heterocyclically substituted phenylsulfonylureas are particularly suitable for use as herbicides or plant growth regulators.

The present invention relates to compounds of the formula (I) (salts),

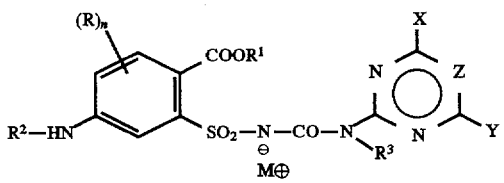

in which n is 0, 1, 2 or 3,

R is halogen, alkyl or alkoxy, namely in each case independently of other substituents R in the event that n is greater than 1, $R^1$ is an unsubstituted or substituted hydrocarbon radical or an unsubstituted or substituted heterocyclic radical, $R^2$ is an acyl radical, $R^3$ is hydrogen or $C_1$–$C_5$-alkyl, $M\oplus$ is a cation equivalent, X and Y independently of one another are halogen, $C_1$–$C_6$-alkyl, $C_1$–$C_6$-alkoxy or $C_1$–$C_6$-alkylthio, each of the three last-mentioned radicals being unsubstituted or substituted by one or more radicals selected from the group consisting of halogen, $C_1$–$C_4$-alkoxy and $C_1$–$C_4$-alkylthio, or are $C_3$–$C_6$-cycloalkyl, $C_2$–$C_6$-alkenyl, $C_2$–$C_6$-alkeynyl, $C_2$–$C_6$-alkenyloxy, $C_2$–$C_6$-alkynyloxy, mono- or di($C_1$–$C_4$-alkyl)amino, and Z is CH or N.

In formula (I) and in all subsequent formulae, the radicals alkyl, alkoxy, haloalkyl, haloalkoxy, alkylamino and alkylthio and the corresponding unsaturated and/or substituted radicals in the hydrocarbon skeleton can in each case be straight-chain or branched. Unless specifically indicated, preferred radicals amongst these are the lower carbon skeletons, for example having 1 to 4 carbon atoms or, in the case of unsaturated groups, 2 to 4 carbon atoms. Alykyl radicals, also in the composite meanings such as alkoxy, haloalykyl and the like are, for example, methyl, ethyl, n- or i-propyl, n-, i-, t- or 2-butyl, pentyl radicals, hexyl radicals such as n-hexyl, i-hexyl and 1,3-dimethylbutyl, heptyl radicals such as n-heptyl, 1-methylhexyl and 1,4-dimethylpentyl; alkenyl and alkynyl radicals have the meaning of the possible unsaturated radicals which correspond to the alkyl radicals; alkenyl is, for example, allyl, 1-methylprop-2-en-1-yl, 2-methylprop-2-en-1-yl, but-2-en-1-yl, but-3-en-1-yl, 1-methyl-but-3-en-1-yl and 1-methylbut-2-en-1-yl; alkynyl is, for example, propargyl, but-2-yn-1-yl, but-3-yn-1-yl and 1-methyl-but-3-yn-1-yl.

Halogen is, for example, fluorine, chlorine, bromine or iodine. Haloalkyl, haloalkenyl and haloalkynyl are alkyl, alkenyl and alkynyl, each of which is partially or fully substituted by halogen, preferably by fluorine, chlorine and/or bromine, in particular by fluorine or chlorine, and is, for example, $CF_3$, $CHF_2$, $CH_2F$, $CF_3CF_2$, $CH_2FCHCl$, $CCl_3$, $CHCl_2$ or $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; the same applies analogously to haloalkenyl and other halogen-substituted radicals.

A hydrocarbon radical is a straight-chain, branched or cyclic and saturated or unsaturated aliphatic or aromatic hydrocarbon radical, for example alkyl, alkenyl, alkynyl, cycloalkyl, cycloalkenyl or aryl; aryl is a mono-, di- or polycyclic aromatic system, for example phenyl, naphthyl, tetrahydronaphthyl, indenyl, indanyl, pentalenyl, fluorenyl and the like, preferably phenyl; a hydrocarbon radical is preferably alkyl, alkenyl or alkynyl having up to 12 carbon atoms or cycloalkyl having 5 or 6 ring atoms, or phenyl;

A heterocyclic radical or ring can be saturated, unsaturated or heteroaromatic; it has one or more hetero ring atoms, preferably selected from the group consisting of N, O and S; for example, it has 3 to 8 ring atoms; it is preferably 5- or 6-membered and has 1, 2 or 3 hetero ring atoms. For example, the heterocyclic radical can be a heteroaromatic radical or ring (heteroaryl), such as, for example, a mono-, di- or polycyclic aromatic system in which at least 1 ring has one or more hetero atoms, for example pyridyl, pyrimidinyl, pyridazinyl, pyrazinyl, thienyl, thiazolyl, oxazolyl, furyl, pyrrolyl, pyrazolyl and imidazolyl, or it is a partially or fully hydrogenated radical such as oxiranyl, pyrrolidyl, piperidyl, piperazinyl, dioxolanyl, morpholinyl or tetrahydrofuryl. Suitable substituents for a substituted heterocyclic radical are the substituents mentioned further below, and additionally also oxo. The oxo group can also occur on those hetero ring atoms of which various degrees of oxidation are possible, for example in the case of N and S.

Substituted radicals, such as substituted hydrocarbon radicals, for example substituted alkyl, alkenyl, alkynyl, aryl, phenyl and benzyl, or substituted heteroaryl, are, for example, a substituted radical which is derived from the unsubstituted parent structure, it being possible, in principle, for the substituents to be selected from a wide range of radicals which differ greatly with regard to their structure; substituents on the parent structure are, for example, functional groups, including hydrocarbon radicals or heterocyclic radicals which are bound in each case to the parent structure via hetero atoms or other functional groups, or they are carbocyclic or heterocyclic radicals which are bound directly to the parent structure or, in the case of cyclic parent structures, also acyclic hydrocarbon radicals which are bound directly to the parent structure. In principle, the substituents mentioned can be further substituted. Substituents on the parent structure are, for example, one or more, preferably 1, 2 or 3, radicals selected from the group consisting of halogen, alkoxy, haloalkoxy, alkylthio, hydroxy, amino, nitro, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl, and, in the case of cyclic parent structures, also alkyl and haloalkyl, as well as unsaturated aliphatic radicals, such as alkenyl, alkynyl, alkenyloxy, alkynyloxy and the like, which correspond to the above-mentioned saturated hydrocarbon-containing radicals; preferred amongst the radicals which halve carbon atoms are those having 1 to 4 carbon atoms, in particular 1 or 2 carbon atoms. As a rule, preferred substituents are those selected from the group consisting of halogen, for example fluorine and chlorine, $C_1$–$C_4$-alkyl, preferably methyl or ethyl, $C_1$–$C_4$-haloalkyl, preferably trifluoromethyl, $C_1$–$C_4$-alkoxy, preferably methoxy or ethoxy, $C_1$–$C_4$-haloalkoxy, nitro and cyano. Particularly preferred are the substituents methyl, methoxy and chlorine. Other examples of substituents on the parent structure are heterocyclic radicals, preferably saturated heterocyclic radicals having 3 to 6 ring atoms and an oxygen atom as the hetero ring atom, and these heterocyclic radicals can additionally be substituted by further substituents such as, for example, $C_1$–$C_4$-alkyl.

Optionally substituted phenyl is preferably phenyl which is unsubstituted or mono- or polysubstituted, preferably up to trisubstituted, by identical or different radicals selected from the group consisting of halogen, $C_1$–$C_4$-alkyl, $C_1$–$C_4$-alkoxy, $C_1$–$C_4$-haloalkyl, $C_1$–$C_4$-haloalkoxy and nitro, for example o-, m- and p-tolyl, dimethylphenyl radicals, 2-, 3- and 4-chlorophenyl, 2-, 3- and 4-tri-fluoro- and -trichlorophenyl, 2,4-, 3,5-, 2,5- and 2,3-dichlorophenyl, and o-, m- and p-methoxyphenyl.

An acyl radical is the radical of an organic acid, for example the radical of a carboxylic acid and radicals of acids derived therefrom, such as thiocarboxylic acid, optionally nitrogen-substituted iminocarboxylic acids, or the radical of carbonic monoesters, optionally nitrogen-substituted carbamic acid, sulfonic acids, sulfinic acids, phosphonic acids, phosphinic acids. Acyl is, for example, formyl, alkylcarbonyl such as ($C_1$–$C_4$-alkyl)carbonyl, phenylcarbonyl, it being possible for the phenyl ring to be substituted, for example as shown above for phenyl, or alkoxycarbonyl, phenoxycarbonyl, benzoxycarbonyl, alkylsulfonyl, alkylsulfinyl, N-alkyl-1-iminoalkyl and other radicals of organic acids.

The invention also relates to all stereoisomers which are embraced by formula (I), and to mixtures of these. Such compounds of the formula (I) have one or more asymmetric carbon atoms or else double bonds, which are not mentioned specifically in the formulae (I). The stereoisomers which are possible, defined by their specific spatial form, such as enantiomers, diastereomers and Z and E isomers, are all embraced by the formula (I) and can be obtained by customary methods from mixtures of the stereoisomers, or else prepared by stereoselective reactions in combination with the use of stereochemically pure starting materials.

The compounds of the formula (I) are salts in which the cation is preferably a cation which can be used in the field of agriculture. Examples of these salts are metal salts, preferably alkali metal salts or alkaline earth metal salts, in particular sodium and potassium salts, or else ammonium salts and ammonium salts which are substituted by organic radicals.

Compounds of the formula (I) according to the invention which are of particular interest are those in which n is 0, 1 or 2, preferably 0 and 1, in particular 0, R is halogen, $C_1$–$C_3$-alkyl or $C_1$–$C_3$-alkoxy, $R^1$ is an aliphatic or cycloaliphatic hydrocarbon radical having up to 24 carbon atoms which is unsubstituted or substituted, or an unsubstituted or substituted saturated heterocyclic radical having 3 to 6 ring atoms, preferably $C_1$–$C_6$-alkyl, $C_2$–$C_6$-alkenyl, $C_2$–$C_6$-alkynyl or $C_3$–$C_6$-cycloalkyl, each of the four last-mentioned radicals being unsubstituted or substituted by one or more radicals selected from the group consisting of halogen, CN, $C_1$–$C_4$-alkoxy, $C_1$–$C_4$-haloalkoxy, mono-($C_1$–$C_4$-alkyl)amino, di($C_1$–$C_4$-alkyl)amino, $C_1$–$C_4$-alkylsulfonyl, $C_1$–$C_4$-alkylsulfinyl, ($C_1$–$C_4$-alkoxy)carbonyl, aminocarbonyl, mono($C_1$–$C_4$-alkyl)aminocarbonyl, di($C_1$–$C_4$-alkyl)aminocarbonyl, unsubstituted phenyl, substituted phenyl, unsubstituted heterocyclic radical and substituted heterocyclic radical, or is a heterocyclic radical having 3, 4, 5 or 6 ring atoms and an oxygen atom as hetero ring atom, the radical being unsubstituted or substituted by one or more radicals selected from the $C_1$–$C_4$-alkyl group, $R^2$ is CO—$R^4$, CO—$OR^5$, CO—$NR^6R^7$ or $SO_2$—$R^8$, $R^3$ is H or $C_1$–$C_4$-alkyl, $R^4$ is hydrogen, $C_1$–$C_6$-alkyl, $C_2$–$C_6$-alkenyl, $C_2$–$C_6$-alkynyl, $C_3$–$C_6$-cycloalkyl, each of the four last-mentioned radicals being unsubstituted or substituted by one or more radicals selected from the group consisting of halogen, CN, $C_1$–$C_4$-alkoxy, $C_1$–$C_4$-haloalkoxy, mono($C_1$–$C_4$-alkyl)amino, di($C_1$–$C_4$-alkyl)amino, $C_1$–$C_4$-alkylsulfonyl, $C_1$–$C_4$-alkylsulfinyl, ($C_1$–$C_4$-alkoxy)carbonyl, aminocarbonyl, mono($C_1$–$C_4$-alkyl)aminocarbonyl, di($C_1$–$C_4$-alkyl)aminocarbonyl, phenyl and substituted phenyl, or is phenyl which is unsubstituted or substituted, $R^5$ is analogous to $R^4$, with the exception of hydrogen, $R^6$ and $R^7$ independently of one another are H, $C_1$–$C_6$-alkyl, $C_2$–$C_6$-alkenyl, $C_2$–$C_6$-alkynyl, each of the three last-mentioned radicals being unsubstituted or substituted by one or more radicals selected from the group consisting of halogen, such as F, Cl and Br, and CN, $C_1$–$C_4$-alkoxy, $C_1$–$C_4$-haloalkoxy, mono($C_1$–$C_4$-alkyl)amino, di($C_1$–$C_4$-alkyl)amino, $C_1$–$C_4$-alkylsulfonyl, $C_1$–$C_4$-alkylsulfinyl, ($C_1$–$C_4$-alkoxy)carbonyl, aminocarbonyl, mono($C_1$–$C_4$-alkyl)aminocarbonyl and di($C_1$–$C_4$-alkyl)aminocarbonyl, or $R^6$ and $R^7$ together with the nitrogen atom to which they are bonded are an unsubstituted or substituted heterocyclic ring of four to eight ring atoms which has up to 18 carbon atoms inclusive of the substituents, preferably up to 12 carbon atoms, $R^8$ is $C_1$–$C_5$-alkyl or $C_2$–$C_5$-alkenyl, each of the two last-mentioned radicals being unsubstituted or substituted by one or more radicals selected from the group consisting of halogen, $C_1$–$C_4$-alkoxy, $C_1$–$C_4$-haloalkoxy, mono($C_1$–$C_4$-alkyl)amino and di($C_1$–$C_4$-alkyl)amino, $M^\oplus$ is the cation equivalent of an alkali metal or alkaline earth metal, such as $Na^+$, $K^+$, $½Mg^{2+}$ and $½Ca^{2+}$, or $NH_4^+$, $½Zn^{2+}$, $R°NH_3^+$, $R°_2NH_2^+$, $R°_3NH^+$ or $R°_4N^+$, $R°$ is $C_1$–$C_6$-alkyl or benzyl, X and Y independently of one another are halogen, $C_1$–$C_4$-alkyl, $C_1$–$C_4$-alkoxy or $C_1$–$C_4$-alkylthio, each of the three last-mentioned radicals being unsubstituted or substituted by one or more radicals selected from the group consisting of halogen, $C_1$–$C_4$-alkoxy and $C_1$–$C_4$-alkylthio, or are mono- or di($C_1$–$C_4$-alkyl)-amino, $C_3$–$C_6$-cycloalkyl, $C_2$–$C_5$-alkenyl or $C_2$–$C_5$-alkynyloxy, and Z is CH or N.

Preferred compounds of the formula (I) according to the invention are those in which $R^1$ is $C_1$–$C_6$-alkyl, $C_2$–$C_6$-alkenyl, $C_2$–$C_6$-alkynyl or $C_3$–$C_6$-cycloalkyl, each of the four last-mentioned radicals being unsubstituted or substituted by one or more radicals selected from the group consisting of F, Cl, Br, I, CN, $OCH_3$, $OCF_3$, $N(CH_3)_2$, $SO_2CH_3$, $CO_2CH_3$, $CO_2N(CH_3)_2$ and phenyl, or is a radical of the formulae $A_1$ to $A_7$

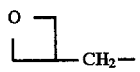 ($A_1$)

 ($A_2$)

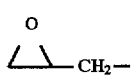 ($A_3$)

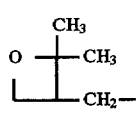 ($A_4$)

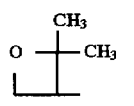 ($A_5$)

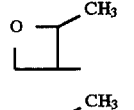 ($A_6$)

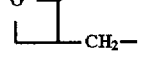 ($A_7$)

$R^2$ is $CO-R^4$, $CO-OR^5$, $CO-NR^6R^7$ or $SO_2-R^8$,
$R^3$ is H or $CH_3$,
$R^4$ is hydrogen, $C_1-C_6$-alkyl, $C_2-C_6$-alkenyl, $C_2-C_6$-alkynyl or $C_3-C_6$-cycloalkyl, each of the four
$OCH_2CF_3$, in particular $OCH_3$, Me or Cl, or
a combination of the above preferred radicals.

Particularly preferred compounds of the formula (I) are those in which
$R^1$ is $CH_3$,
$R^2$ is $CO-CH_3$, $CO-CH_2CH_3$, isopropyl-carbonyl, cyclopropyl-carbonyl, $COOCH_3$, $COOC_2H_5$, in particular $COCH_3$, $COCH_2CH_3$ or $COOCH_3$,
$R^3$ is H,
one of the radicals X and Y
is halogen, $C_1-C_2$-alkyl, $C_1-C_2$-alkoxy or $C_1-C_2$-alkylthio, each of the three last-mentioned radicals being unsubstituted or substituted by one or more radicals selected from the group consisting of halogen, $C_1-C_2$-alkoxy and $C_1-C_2$-alkylthio, or is mono- or di($C_1-C_2$-alkyl)amino, preferably halogen, methyl or methoxy, and
the other of the radicals X and Y is $C_1-C_2$-alkyl, $C_1-C_2$-haloalkyl, $C_1-C_2$-alkoxy, $C_1-C_2$-haloalkoxy or $C_1-C_2$-alkylthio, preferably methyl or methoxy, and
Z is CH or N, preferably CH.

Examples of compounds according to the invention are, in particular, compounds of the formula (I) in which $R^1$ is methyl, $R^2$ is acetyl, $R^3$ is H, X is methoxy, Y is methoxy, Z is CH and $M^+$ is $Na^+$;
$R^1$ is methyl, $R^2$ is acetyl, $R^3$ is H, X is methoxy, Y is methoxy, Z is CH and $M^+$ is $K^+$;
$R^1$ is methyl, $R^2$ is acetyl, $R^3$ is H, X is methoxy, Y is methoxy, Z is CH and $M^+$ is $NH_4^+$;
$R^1$ is methyl, $R^2$ is acetyl, $R^3$ is H, X is methoxy, Y is methyl, Z is CH and $M^+$ is $Na^+$;
$R^1$ is methyl, $R^2$ is acetyl, $R^3$ is H, X is methoxy, Y is methyl, Z is CH and $M^+$ is $K^+$;
$R^1$ is methyl, $R^2$ is acetyl, $R^3$ is H, X is methoxy, Y is methyl, Z is CH and $M^+$ is $NH_4^+$;
$R^1$ is methyl, $R^2$ is acetyl, $R^3$ is H, X is methyl, Y is last-mentioned radicals being unsubstituted or substituted by one or more radicals selected from the group consisting of F, Cl, Br, I, CN, $OCH_3$, $OCF_3$, $N(CH_3)_2$, $SO_2CH_3$, $CO_2CH_3$, $CON(CH_3)_2$ and phenyl, or is phenyl which is unsubstituted or up to tri-substituted by identical or different radicals selected from the group consisting of halogen, $CH_3$, $C_2H_5$, $OCH_3$, $OC_2H_5$, $CF_3$, $C_2H_5Cl$, $OCHF_3$ or $OCHF_2$,
$R^5$ is analogous to $R^4$, with the exception of hydrogen,
$R^6$ and $R^7$ independently of one another are H, $C_1-C_6$-alkyl, $C_2-C_6$-alkenyl or $C_2-C_6$-alkynyl, each of the three last-mentioned radicals being unsubstituted or substituted by one or more radicals selected from the group consisting of F, Cl, Br, CN, $OCH_3$, $OCF_3$, $N(CH_3)_2$, $SO_2CH_3$, $CO_2CH_3$ and $CON(CH_3)_2$, and
$R^8$ is $C_1-C_5$-alkyl or $C_2-C_5$-alkenyl, each of the two last-mentioned radicals being unsubstituted or substituted by one or more radicals selected from the group consisting of F, Cl, Br, $OCH_3$ or $N(CH_3)_2$.

Preferred compounds of the formula (I) according to the invention are those in which
$R^1$ is $C_1-C_6$-alkyl, preferably $CH_3$, or
$R^2$ is $CO-R^4$, preferably CHO, $CO-CH_3$, $CO-CH_2CH_3$, cyclopropyl-carbonyl, isopropyl-carbonyl or t-butylcarbonyl, or
$R^2$ is $CO-OR^5$, preferably $COOCH_3$, $COOC_2H_5$ and $COOCH_2CH_2Cl$, or
$R^2$ is $CO-NR^6R^7$, preferably $CONH_2$, $CONHCH_3$, $CO-NH-C_2H_5$ or $CON(CH_3)_2$, or
$R^2$ is $SO_2-R^8$, preferably $SO_2CH_3$, $SO_2C_2H_5$, $SO_2CH_2F$ or $SO_2CH_2Cl$, or
$R^3$ is H, or
$M\oplus$ is $Na^+$, $K^+$, $½Mg^{2+}$, $½Ca^{2+}$, $NH_4^+$, $H_2NEt_2^+$, $H_3NC_4H_9^+$, $NH(C_2H_5)_3^+$, $N(C_2H_5)_4^+$, $N(CH_3)_4^+$, $HN(CH_3)_3^+$, preferably $Na^+$, $K^+$, $½Mg^{2+}$, $½Ca^{2+}$, $NH_4^+$, $NH(C_2H_5)_3^+$, or
$R^\circ$ is $C_1-C_6$-alkyl, preferably isopropyl, methyl, ethyl, n-propyl or n-butyl, or
X and Y are $OCH_3$, $OC_2H_5$, $SCH_3$, $NHCH_3$, $N(CH_3)_2$, $CH_3$, is methyl, Z is CH and $M^+$ is $Na^+$;
$R^1$ is methyl, $R^2$ is acetyl, $R^3$ is H, X is methyl, Y is methyl, Z is CH and $M^+$ is $K^+$;
$R^1$ is methyl, $R^2$ is acetyl, $R^3$ is H, X is methyl, Y is methyl, Z is CH and $M^+$ is $NH_4^+$;
$R^1$ is methyl, $R^2$ is propionyl, $R^3$ is H, X is methoxy, Y is methoxy, Z is CH and $M^+$ is $Na^+$;
$R^1$ is methyl, $R^2$ is propionyl, $R^3$ is H, X is methoxy, Y is methyl, Z is CH and $M^+$ is $Na^+$;
$R^1$ is methyl, $R^2$ is propionyl, $R^3$ is H, X is methyl, Y is methyl, Z is CH and $M^+$ is $Na^+$;
$R^1$ is methyl, $R^2$ is acetyl, $R^3$ is H, X is methoxy, Y is methoxy, Z is CH and $M^+$ is $NH(C_2H_5)_3^+$;
$R^1$ is methyl, $R^2$ is acetyl, $R^3$ is H, X is methoxy, Y is methoxy, Z is CH and $M^+$ is $N(CH_3)_4^+$;
$R^1$ is methyl, $R^2$ is methoxycarbonyl, $R^3$ is H, X is methoxy, Y is methoxy, Z is CH and $M^+$ is $Na^+$;
$R^1$ is methyl, $R^2$ is methoxycarbonyl, $R^3$ is H, X is methoxy, Y is methoxy, Z is CH and $M^+$ is $K^+$;
$R^1$ is methyl, $R^2$ is methoxycarbonyl, $R^3$ is H, X is methoxy, Y is methoxy, Z is CH and $M^+$ is $NH_4^+$;
$R^1$ is methyl, $R^2$ is methoxycarbonyl, $R^3$ is H, X is methoxy, Y is methyl, Z is CH and $M^+$ is $Na^+$;

$R^1$ is methyl, $R^2$ is methoxycarbonyl, $R^3$ is H, X is methoxy, Y is methyl, Z is CH and $M^+$ is $K^+$;

$R^1$ is methyl, $R^2$ is methoxycarbonyl, $R^3$ is H, X is methoxy, Y is methyl, Z is CH and $M^+$ is $NH_4^+$;

$R^1$ is methyl, $R^2$ is methoxycarbonyl, $R^3$ is H, X is methyl, Y is methyl, Z is CH and $M^+$ is $Na^+$;

$R^1$ is methyl, $R^2$ is methoxycarbonyl, $R^3$ is H, X is methyl, Y is methyl, Z is CH and $M^+$ is $K^+$;

$R^1$ is methyl, $R^2$ is methoxycarbonyl, $R^3$ is H, X is methyl, Y is methyl, Z is CH and $M^+$ is $NH_4^+$;

$R^1$ is methyl, $R^2$ is ethoxycarbonyl, $R^3$ is H, X is methoxy, Y is methoxy, Z is CH and $M^+$ is $Na^+$;

$R^1$ is methyl, $R^2$ is ethoxycarbonyl, $R^3$ is H, X is methoxy, Y is methyl, Z is CH and $M^+$ is $Na^+$;

$R^1$ is methyl, $R^2$ is ethoxycarbonyl, $R^3$ is H, X is methyl, Y is methyl, Z is CH and $M^+$ is $Na^+$;

$R^1$ is methyl, $R^2$ is methoxycarbonyl, $R^3$ is H, X is methoxy, Y is methoxy, Z is CH and $M^+$ is $NH(C_2H_5)_3^+$;

$R^1$ is methyl, $R^2$ is methoxycarbonyl, $R^3$ is H, X is methoxy, Y is methoxy, Z is CH and $M^+$ is $N(CH_3)_4^+$;

The present invention furthermore provides processes for the preparation of the compounds of the formula (I) according to the invention, which comprise reacting a compound of the formula (II)

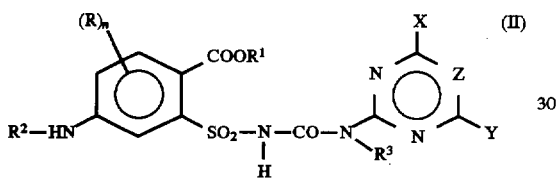

with a suitable base of the formula (III)

$$M^\oplus X^\ominus \quad (III)$$

in which $X^\ominus$ is an anion equivalent, for example $^\ominus OH$, $\frac{1}{2}CO_3^{2\ominus}$, $^\ominus O\text{—}(C_1\text{-}C_4)\text{-alkyl}$, $^\ominus O\text{—}Ar$ or $H^\ominus$, and $M^\oplus$ is as defined in the abovementioned formula (I), and Ar is aryl, or, in the case of an ammonium salt, reacting the compound correspondingly with ammonia or with an organic amine, preferably with a compound of the formula (IV)

$$H_m NR^\circ_{3-m} \quad (IV)$$

in which m is 0, 1, 2 or 3 and $R^\circ$ is as defined in formula (I).

The reaction of the compounds (II) with the bases of the formula (III) or the amines of the formula (IV) to give the salts of the formula (I) is preferably carried out in inert solvents such as, for example, dichloromethane, acetonitrile, dioxane, tetrahydrofuran (THF), N-methylpyrrolidine, dimethylformamide, dimethylacetamide, water or alcohols such as, for example, methanol, ethanol or isopropanol, or else in solvent mixtures at temperatures from –20° C. to the boiling point of the solvent in question, preferably from –10° to 80° C.

The salts of the formula (I) may also be synthesized from the sulfonylureas (II) by adding suitable bases to the formulation auxiliaries or in the tank mix, i.e. the compounds of the formula (I) are only formed from the sulfonylureas of the formula (II) in the tank mix, either during the formulation process or shortly before application.

The compounds of the formula (II) are known from the literature mentioned further above or can be prepared analogously to the processes described therein.

The reaction sequences (1) to (8) below are examples of various possibilities of preparing the intermediates of the formula (II):

Equation 1: Synthetic route for obtaining compounds of the formula (II)

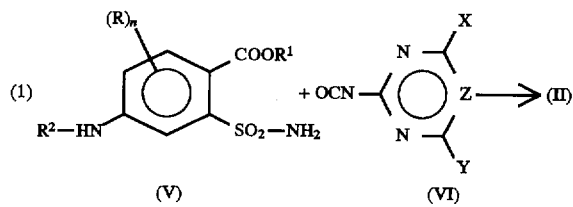

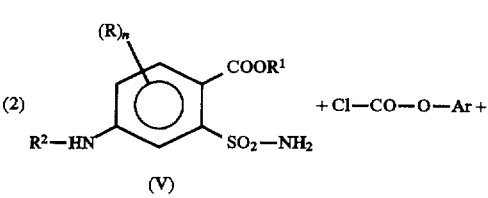

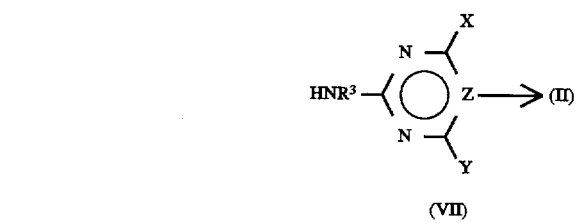

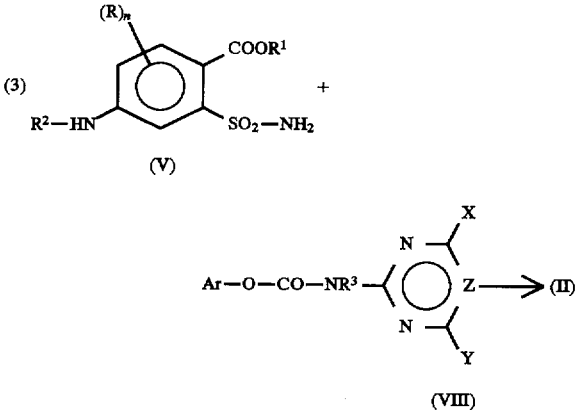

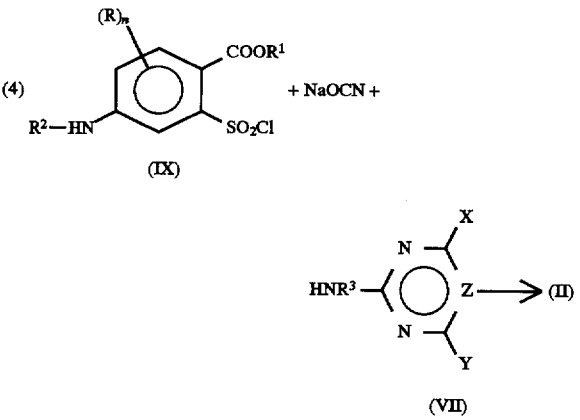

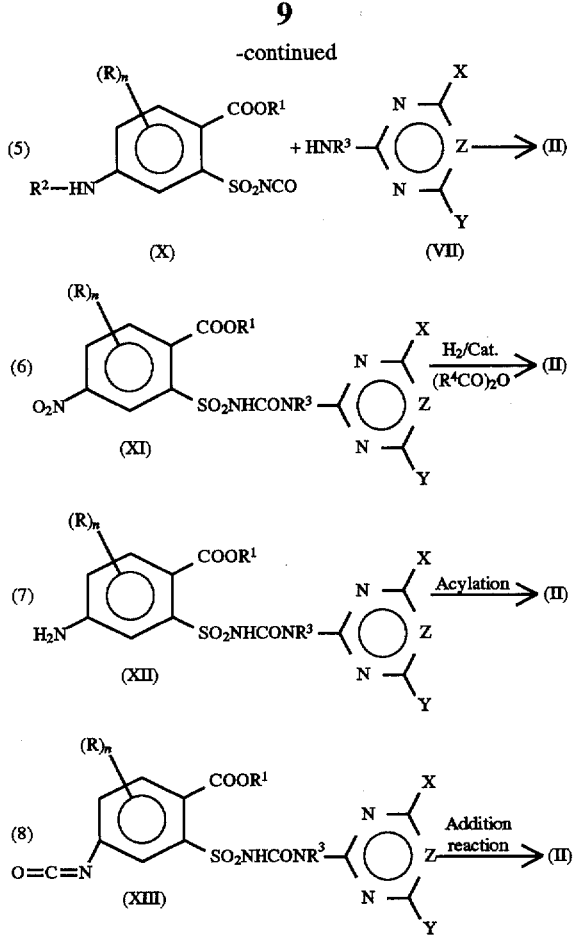

In formulae (V)–(XIII), R, R¹, R², R³, X, Y, Z and n are as defined in (II), R² in reaction sequence (6) being COR⁴ and it being necessary for the acylating reagent, or addition reagent, in reaction sequences (7) and (8) to be selected in the customary manner, depending on the meaning of R².

Compounds of the formula (V) are reacted with isocyanates of the formula (VI) in analogy to processes known from the literature (EP-A-232 067, EP-A-166 516) at −10° C. to 150° C., preferably 20° to 100° C., in an inert solvent such as, for example, acetone or acetonitrile, in the presence of a suitable base, such as, for example, triethylamine or potassium carbonate (Equation 1, (1)).

The reaction of the sulfonamides of the formula (V) with aryl chloroformate and heterocyclic amines (VII) gives the sulfonylureas (II) (cf. U.S. Pat. No. 4,994,571). First, the sulfonamides (V) and, for example, phenyl chloroformate are reacted in the presence of a suitable base such as, for example, triethylamine or potassium carbonate, to give the corresponding sulfonylcarbamates (XIV). The compounds (XIV) can be reacted with heterocyclic amines to give the sulfonylureas (II) (Equation 1, (2)).

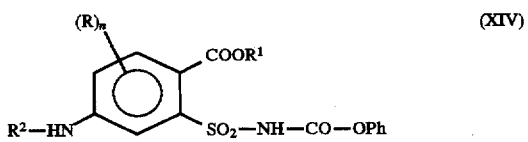

Heterocyclic carbamates of the formula (VIII) react with sulfonamides (II) in the presence of suitable bases such as, for example, organic-nitrogen bases (for example 1,8-diazabicyclo[5.4.0]undec-7-ene (DBU) or triethylamine), carbonates (for example potassium carbonate, sodium carbonate), alcoholates (for example sodium methanolate, sodium ethanolate) or phenolates (for example sodium phenolate) in inert solvents such as, for example, acetonitrile, methylene chloride, dioxane or THF, at temperatures from −10° C. to the boiling point of the solvent in question. The carbamates required for the reaction are known from the literature or can be prepared analogously to known processes (cf. EP-A-70 804; U.S. Pat. No. 4,480,101; EP-A-562 575; EP-A-562 576) (see Equation 1, (3)).

The reaction of the sulfonyl chlorides (IX) with the amino heterocycles of the formula (VII) and cyanates, such as sodium cyanate and potassium cyanate, is carried out for example in aprotic solvents such as, for example, acetonitrile, if appropriate in the presence of bases, for example 0.5 to 2 equivalents of base, or in basic aprotic solvents at temperatures between −10° and 100° C., preferably between −10° and 60° C., in particular 15° to 40° C. Suitable bases or basic aprotic solvents are, for example, pyridine, picoline or lutidine, or a mixture of these (cf. U.S. Pat. No. 5,157,119) (Equation 1, (4)).

The phenylsulfonyl isocyanates of the formula (X) can be prepared from compounds of the formula (V), for example with phosgene, for example analogously to the process of EP-A-184 385. The reaction of the compounds (X) with the amino heterocycles of the formula (VII) is preferably carried out in inert aprotic solvents such as, for example, dioxane, acetonitrile or tetrahydrofuran, at temperatures between 0° C. and the boiling point of the solvent (Equation 1, (5)).

The abovementioned syntheses of the sulfonylureas of the formula (II) in accordance with Equation 1, (1) to (5) are novel and also provided by the invention. The invention also provides a process for the preparation of the intermediates of the formula (II) which comprises subjecting a nitro-substituted phenylsulfonylurea of the abovementioned formula (XI) to catalytic hydrogenation on the nitro group in the presence of an acylating agent of the formula $(R^4CO)_2O$ and reacting the product with the acylating agent (Equation 1, (6)).

The catalytic hydrogenation of the nitro group can be carried out with hydrogen in the presence of a suitable hydrogenation catalyst, for example of group VIII of the Periodic Table, such as Ni, Pd, Pt and Rh, analogously to customary conditions for catalytic hydrogenations, but in the presence of the acylating agent with which the nitro group, which has been reduced to an amino group, is to be acylated. The process is carried out for example by stirring a suspension of the compound of the formula (XI) in a suitable anhydride, such as, for example, acetic anhydride, and a suitable catalyst such as, for example, Raney nickel or palladium on charcoal, under a hydrogen atmosphere of an $H_2$ pressure of, for example, 1 to 100 atm, preferably an $H_2$ pressure of 1 to 10 atm. The reaction can also be carried out with an addition of inert solvents, such as, for example, acetic acid, propionic acid, dimethylformamide, N-methylpyrrolidone or acetic dimethylamide. The hydrogenolysis of the nitro group of compounds (XI) in the presence of acid anhydrides (Equation 1, (6)) allows the sulfonylureas (II) to be prepared by a novel and inventive process, which represents an advantageously short synthetic route affording surprisingly high yields.

Additionally, there exist two other processes for obtaining compounds of the formula (II); see Equation 1, (7) and (8). These processes are described in the literature (U.S. Pat. No. 4,892,946).

The abovementioned eight processes for the synthesis of compounds of the formula (II) (Equation 1) can be combined directly with the deprotonation step to prepare the salts of the formula (I), for example by isolating the salts of the formula (I) from a basic reaction medium instead of the neutral compounds of the formula (II), which are obtained from a neutral or acidic reaction medium. Suitable one-pot syntheses are characterized, for example, by the addition of suitable bases, such as, for example, $Na_2CO_3$, NaOH, $NaOCH_3$, and the like, to the reaction mixtures obtained from synthesizing compounds of the formula (II), and subsequently isolating the salts of the formula (I). These processes for directly obtaining the compounds of the formula (I) are also novel and provided by the present invention.

The "inert solvents" mentioned in the above process variants are in each case to be understood as meaning solvents which are inert under the reaction conditions in question, but which do not have to be inert under any desired reaction conditions.

The compounds of the formula (I) according to the invention have an excellent herbicidal activity against a broad spectrum of economically important monocotyledon and dicotyledon harmful plants. The active substances also act efficiently on perennial weeds which produce shoots from rhizomes, root stocks or other perennial organs and which are difficult to control. In this context, it does not matter whether the substances are applied before sowing, pre-emergence or post-emergence. Specifically, examples may be mentioned of some representatives of the monocotyledon and dicotyledon weed flora which can be controlled by the compounds according to the invention, without the enumeration being taken to mean a restriction to certain species.

Examples of weed species on which the active substance acts efficiently are, from amongst the monocotyledon weed species, Arena, Lolium, Alopecurus, Phalaris, Echinochloa, Digitaria, Setaria and also Cyperus species from the annual sector and from amongst the perennial species Agropyron, Clmodon, Imperata and Sorghum, and also perennial Cyperus species. In the case of the dicotyledon weed species, the range of action extends to species such as, for example, Galium, Viola, Veronica, Lamium, Stellaria, Amaranthus, Sinapis, Ipomoea, Matricaria, Abutilon and Sida from amongst the annuals, and Convolvulus, Cirsium, Rumex and Artemisia in the case of the perennial weeds.

The active substances according to the invention also effect an outstanding control of weeds which occur under the specific conditions of rice growing, such as, for example, Sagittaria, Alisma, Eleocharis, Scirpus and Cyperus.

If the compounds according to the invention are applied to the soil surface before germination, then the weed seedlings are either prevented completely from emerging, or the weeds grow until they have reached the cotyledon stage but then their growth stops and, eventually, after three to four weeks have elapsed, they die completely.

When the active substances are applied post-emergence to the green parts of the plants, growth stops equally drastically a very short time after treatment and the weed plants remain at the stage of growth at the time of application, or they die completely after a certain time, so that in this manner competition by the weeds, which is harmful to the crop plants, is eliminated at a very early stage and in a sustained manner.

Even though the compounds according to the invention have an excellent herbicidal activity against monocotyledon and dicotyledon weeds, crop plants of economically important crops, such as, for example, wheat, barley, rye, rice, maize, sugar beet, cotton and soya, are damaged only to a negligible extent, or not at all. For these reasons, the present compounds are highly suitable for selectively controlling undesired vegetation in crops of agriculturally useful plants.

Moreover, the substances according to the invention exhibit outstanding growth-regulating properties in crop plants. They engage in the plant metabolism in a regulating manner and can thus be used for targeted plant constituent control and for facilitating harvesting, for example by provoking desiccation and stunted growth. Moreover, they are also suitable for generally controlling and inhibiting undesirable vegetative growth, without destroying the plants at the same time. Inhibition of the vegetative growth plays an important role in a large number of monocotyledon and dicotyledon crops, since it allows lodging to be reduced or prevented completely.

The compounds according to the invention can be used in the customary preparations in the form of wettable powders, emulsifiable concentrates, sprayable solutions, dusts or granules. The invention therefore also provides herbicidal and plant growth-regulating compositions comprising the compounds of the formula (I).

The compounds of the formula (I) can be formulated in a variety of ways, as determined by the prevailing biological and/or chemical-physical parameters. The following possibilities are therefore suitable for formulation: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for broadcasting and soil application, granules (GR) in the form of microgranules, spray granules, coating granules and adsorption granules, water-dispersible granules (WG), water-soluble granules (SC), ULV formulations, microcapsules and waxes.

These individual formulation types are known in principle and are described, for example, in: Winnacker-Küchler, "Chemische Technologie" [Chemical Technology], Volume 7, C. Hauser Verlag Munich, 4th ed., 1986, Wade van Valkenburg, "Pesticide Formulations", Marcel Dekker, New York, 1973; K. Martens, "Spray Drying" Handbook, 3rd ed. 1979, G. Goodwin Ltd. London.

The formulation auxiliaries required, such as inert materials, surfactants, solvents and other additives, are also known and are described, for example, in: Watkins, "Handbook of Insecticide Dust Diluents and Carriers", 2nd ed., Darland Books, Caldwell N. J., H. v. Olphen, "Introduction to Clay Colloid Chemistry"; 2nd ed., J. Wiley & Sons, New York; C. Marsden, "Solvents Guide"; 2nd ed.; Interscience, New York 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., New York 1964; Schönfeldt, "Grenzfl achenaktive Äthylenoxidaddukte" [Surface-Active Ethylene Oxide Adducts], Wiss. Verlagsgesell., Stuttgart 1976; Winnacker-Küchler, "Chemische Technologie" [Chemical Technology], Volume 7, C. Hauser Verlag Munich, 4th ed. 1986.

Combinations with other pesticidally active substances, such as, for example, insecticides, acaricides, other herbicides, fungicides, safeners, fertilizers and/or growth regulators, may also be prepared on the basis of these formulations, for example in the form of a readymix or a tank mix.

Wettable powders are preparations which are uniformly dispersible in water and which, besides the active substance, also comprise ionic and/or non-ionic surfactants (wetting agents, dispersants), for example polyethoxylated alkylphenols, polyethoxylated fatty alcohols, polyethoxylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, in addition to a diluent or inert substance. To prepare the wettable powders, the herbicidal active substances are ground finely, for example in customary apparatus such as hammer mills, blower mills and air-jet mills, and simultaneously or subsequently mixed with the formulation auxiliaries.

Emulsifiable concentrates are prepared by dissolving the active substance in an organic solvent, for example butanol, cyclohexanone, dimethylformamide, xylene or else higher-boiling aromatics or hydrocarbons or mixtures of the organic solvents, with addition of one or more ionic and/or non-ionic surfactants (emulsifiers). Examples of emulsifiers which can be used are: calcium alkylarylsulfonates, such as calcium dodecylbenzenesulfonate, or non-ionic emulsifiers such as fatty acid polyglycol esters, alkylaryl polyglycol ethers, fatty alcohol polyglycol ethers, propylene oxide/ethylene oxide condensation products, alkyl polyethers, sorbitan esters, such as, for example, sorbitan fatty acid esters or polyoxyethylene sorbitan esters, such as, for example, polyoxyethylene sorbitan fatty acid esters.

Dusts are obtained by grinding the active substance with finely divided solid substances, for example talc, natural clays such as kaolin, bentonite or pyrophyllite, or diatomaceous earth.

Suspension concentrates can be oil- or water-based. They can be prepared for example by wet grinding using commercially available bead mills and, if appropriate, addition of surfactants as already mentioned above for example in the case of the other formulation types.

Emulsions, for example oil-in-water emulsions (EW), can be prepared for example by means of stirrers, colloid mills and/or static mixtures using aqueous organic solvents and, if appropriate, surfactants as already mentioned above for example in the case of other formulation types.

Granules can be prepared either by spraying the active substance onto adsorptive, granulated inert material or by applying active substance concentrates to the surface of carriers such as sand, kaolinites or granulated inert material, by means of binders, for example polyvinyl alcohol, sodium polyacrylate or else mineral oils. Suitable active substances can also be granulated in the manner which is customary for the preparation of fertilizer granules, if desired in the form of a mixture with fertilizers.

As a rule, water-dispersible granules are prepared by the customary processes, such as spray-drying, fluidized-bed granulation, disk granulation, mixing using high-speed stirrers, and extrusion without solid inert material.

As a rule, the agrochemical preparations comprise 0.1 to 99% by weight, in particular 0.1 to 95% by weight, of active substance of the formula (I).

In wettable powders, the active substance concentration is, for example, approximately 10 to 90% by weight, the remainder to 100% by weight being composed of customary formulation components. In the case of emulsifiable concentrates, the active substance concentration can be approximately 1 to 90, preferably 5 to 80, % by weight. Formulations in the form of dusts comprise 1 to 30, preferably, in most cases, 5 to 20% by weight of active substance, sprayable solutions approximately 0.05 to 80, preferably 2 to 50, % by weight of active substance. In the case of water-dispersible granules, the active substance content depends partly on whether the active compound is in solid or liquid form and on which granulation auxiliaries, fillers and the like are being used. In the case of the water-dispersible granules, the active substance content is, for example, between 1 and 95% by weight, preferably between 10 and 80% by weight.

In addition, the abovementioned formulations of active substance comprise, if appropriate, the adhesives, wetting agents, dispersants, emulsifiers, penetrants, preservatives, antifreeze agents, solvents, fillers, carriers, colorants, antifoams, evaporation inhibitors and pH and viscosity regulators which are customary in each case.

Components which can be used in combination with the active substances according to the invention in mixed formulations or in tank mix are, for example, known active substances, as they are described, for example, in Weed Research 26, 441–445 (1986), or "The Pesticide Manual", 9th edition, The British Crop Protection Council, 1990/91, Brachell, England, and the literature cited therein. Examples of active substances which may be mentioned as herbicides which are known from the literature and which can be combined with the compounds of the formula (I) are the following (note: either the common names in accordance with the International Organization for Standardization (ISO) or the chemical name, if appropriate together with a customary code number, of the compounds are given):

acetochlor; acifluorfen; aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazin; aziprotryn; barban; BAS 516 H, i.e. 5-fluoro-2-phenyl-4H-3,1-benzoxazin-4-one; benazolin; benfluralin; benfuresate; bensulfuron-methyl; bensulide; bentazone; benzofenap; benzofluor; benzoylprop-ethyl; benzthiazuron; bialaphos; bifenox; bromacil; bromobutide; bromofenoxim; bromoxyrnil; bromuron; buminafos; busoxinone; butachlor; butamifos; butenachlor; buthidazole; butralin; butylate; carbetamide; CDAA, i.e. 2-chloro-N,N-di-2-propenylacetamide; CDEC, i.e. chloroallyl diethyldithiocarbamate; CGA 184927, i.e. 2-[4-[(5-chloro-3-fluoro-2-pyridlnyl)oxy]-phenoxy]propanoic acid and its 2-propynyl esters chlomethoxyfen; chloramben; chlorazifop-butyl, pirifenop-butyl; chlorbromuron; chlorbufam; chlorfenac; chlorflurecolmethyl; chloridazon; chlorimuron ethyl; chlornitrofen; chlorotoluron; chloroxuron; chlorpropham; chlorsulfuron; chlorthal-dimethyl; chlorthiamid; cinmethylin; cicinosulfuron; clethodim; clomazone; clomeprop; cloproxydim; clopyralid; cyanazine; cycloate; cycloxydim; cycluron; cyperquat; cyrazine; cyprazole; 2,4-DB; dalapon; desmedipham; desmetryn; di-allate; dicamba; dichlobenil; dichlorprop; diclofop-methyl; diethatyl; difenoxuron; difenzoquat; diflufenican; dimefuron; dimethachlor; dimethametryn; dimethazone, clomazon; dimethipin; dimetrasulfuron, cinosulfuron; dinitramine; dinoseb; dinoterb; diphenamid; dipropetryn; diquat; dithiopyr; diuron; DNOC; eglinazine-ethyl; EL 177, i.e. 5-cyano-1-(1,1-dimethylethyl)-N-methyl-3H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; F6285, i.e. 1-[5-(N-methylsulfonyl)amino-2,4-dichlorophenyl]-3-methyl-4-difluoromethyl-1,2,4-triazol-5-one; fenoprop; fenoxan, s. clomazon; fenoxaprop-ethyl; fenuron; flamprop-methyl; flazasulfuron; fluazifop and its ester derivatives; fluchloralin; flumetsulam; N-[2,6-difluorophenyl]-5-methyl-(1,2,4)triazolo[1,5]pyrimidine-2-sulfonamide; flumeturon; flumipropyn; fluorodifen; fluoroglycofen-ethyl; fluridone; flurochloridone; fluroxypyr; flurtamone; fomesafen; fosamine; furyloxyfen; glufosinate; glyphosate; halosaten; haloxyfop and its ester derivatives; hexazinone; Hw 52, i.e. N-(2,3-dichlorophenyl)-4-(ethoxymethoxy) benzamide; imazamethabenz-methyl; imazapyr; imazaquin; imazethamethapyr; imazethapyr; imazosulfuron; ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyldaimuron; metobromuron; metolachlor; metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiazon; oxyfluorfen; paraquat; pebulate; pendimethalin; perfluidone; phenmedipham; phenisopharm; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its ester derivatives; propazine; propham; propyzamide; prosulfalin; prosulfocarb; prynachlor; pyrazolinate; pyrazon; pyrazosulfuron-ethyl; pyrazoxyfen; pyridate; quinclorac; quinmerac; quinofop and its ester derivatives, quizalofop and its ester derivatives; quizalofop-ethyl; quizalofopp-tefuryl; renriduron; daimuron; S 275, i.e. 2-[4-chloro-2-fluoro-5-(2-propynyloxy)phenyl]-4,5,6,7-tetrahydro-2H-indazole; S 482, i.e. 2-[7-fluoro-3,4-dihydro-3-oxo-4-(2-propynyl)-2H-1,4-benzoxazin-6-yl]-4,5,6,7-tetrahydro-1H-isoindole-1,3(2H)-dione; secbumeton; sethoxydim; siduron; simazine; simetryn; SN 106279, i.e. 2-[[7-[2-chloro-4-(trifluoromethyl) phenoxy]-2-naphthalenyl]oxy]propanoic acid and its methyl esters sulfometuron-methyl; sulfazuron; flazasulfuron; TCA; tebutam; tebuthiuron; terbacil; terbucarb; terbuchlor; terbumeton; terbuthylazine; terbutrynl TFH 450, i.e. N,N-diethyl-3-[(2-ethyl-6-methylphenyl) sulfonyl]-1H-1,2,4-triazole-1-carboxamide; thiazafluron; thifensulfuron-methyl; thiobencarb; tiocarbazil; tralkoxydim; tri-allate; triasulfuron; triazofenamide; tribenuron-methyl; triclopyr; tridiphane; trietazine; trifluralin; trimeturon; vernolate; WL 110547, i.e. 5-phenoxy-1-[3-(trifluoromethyl)phenyl]-1H-tetrazole.

For use, the formulations, which are in commercially available form, are, if appropriate, diluted in the customary manner, for example using water in the case of wettable powders, emulsifiable concentrates, dispersions and water-dispersible granules, and these dilute mixtures are subsequently applied to the plants, parts of plants or the agriculturally or industrially exploited soil on which the plants stand or in which they grow or lie as seed. Preparations in the form of dusts, granules for soil application or broadcasting, as well as sprayable solutions are conventionally not diluted any further with inert substances prior to use.

The application rate required of the compounds of the formula (I) varies with the external conditions such as, inter alia, temperature, humidity and the nature of the herbicide used. It can vary within wide limits, for example between 0.001 and 10.0 kg/ha or more of active ingredient, but it is preferably between 0.005 and 5 kg/ha.

A. Chemical Examples

A1) Sodium salt of 5-acetylamino-N-[(4,6-dimethoxypyrimidin-2-yl)aminocarbonyl]-2-methoxycarbonylbenzenesulfonamide (Table 1, No. 1)

12.0 g of 5-acetylamino-N-[(4,6-dimethoxypyrimidin-2-yl)aminocarbonyl]-2-methoxycarbonylbenzenesulfonamide (obtained by the process of U.S. Pat. No. 4,892,946) are introduced into 80 ml of $CH_2Cl_2$, and 26.5 ml of 1N sodium hydroxide solution are added. The clear mixture is concentrated and extracted by stirring with a small amount of methanol. This gives 10.5 g of the title product as a colorless salt having a melting point of 210° to 212° C., with decomposition.

A2) Sodium salt of N-[(4,6-dimethoxypyrimidin-2-yl) aminocarbonyl]-5-formylamino-2-methoxycarbonylbenzenesulfonamide (Table 1, No. 57)

1.40 g of N-[(4,6-dimethoxypyrimidin-2-yl) aminocarbonyl]-5-formylamino-2-methoxycarbonylbenzenesulfonamide are introduced into 20 ml of methanol, and 0.58 ml of 30% sodium methylate solution are added. After the mixture has been stirred for 30 minutes, methanol is distilled off. The residue is dried under a high vacuum. This gives 1.31 g of the desired salt having a melting point of 202° C., with decomposition.

A3) Sodium salt of N-[(4,6-dimethoxypyrimidin-2-yl) aminocarbonyl]-5-methoxycarbonylamino-2-methoxycarbonylbenzenesulfonamide (Table 1, No. 28)

0.5 g of N-[(4,6-dimethoxypyrimidin-2-yl) aminocarbonyl]-5-methoxycarbonylamino-2-methoxycarbonylbenzenesulfonamide are reacted with 0.20 ml of 30% sodium methylate solution in 13 ml of methanol analogously to Example 2 to give the corresponding salt. This gives 0.5 g of the desired compound having a melting point of 173° C. (decomposition).

The compounds described in Table 1 below are obtained analogously.

The following abbreviations are used in Table 1:

No.=Example No.
M.p.=Melting point
Me=methyl
Et=ethyl
Pr=$^n$Pr=n-propyl
$^i$Pr=i-propyl
$^c$Pr=cyclopropyl
$^t$Bu=tert-butyl
(dec.)=decomposition

TABLE 1

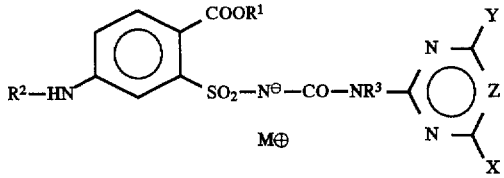

| No. | R¹ | R² | R³ | M | X | Y | Z | m.p. [°C.] |
|---|---|---|---|---|---|---|---|---|
| 1 | Me | CO—Me | H | Na | OMe | OMe | CH | 210–212 (dec.) |
| 2 | Me | CO—Me | H | K | OMe | OMe | CH | |
| 3 | Me | CO—Me | H | HNEt₃ | OMe | OMe | CH | |
| 4 | Me | CO—Me | H | NMe₄ | OMe | OMe | CH | |
| 5 | Me | CO—Me | H | NH₄ | OMe | OMe | CH | |
| 6 | Me | CO—Me | H | Na | OMe | Me | CH | |
| 7 | Me | CO—Me | H | Na | Me | Me | CH | |
| 8 | Me | CO—Me | H | Na | Cl | OMe | CH | |
| 9 | Me | CO—Me | H | K | Cl | OMe | CH | |
| 10 | Me | CO—Me | H | Na | Me | OMe | N | |
| 11 | Me | CO—Me | H | K | Me | OMe | N | |
| 12 | Me | CO—Me | H | Na | OMe | OMe | N | |
| 13 | Me | CO—Me | H | K | OMe | OMe | N | |
| 14 | Me | CO—Me | H | Na | NMe₂ | OCH₂CF₃ | N | |
| 15 | Me | CO—Me | Me | Na | OMe | OMe | CH | |
| 16 | Me | CO—Me | Me | Na | OMe | Me | N | |
| 17 | Me | CO—Et | H | Na | OMe | OMe | CH | 205 (dec.) |
| 18 | Me | CO—Et | H | Na | Cl | OMe | CH | |
| 19 | Me | CO—Et | H | Na | Me | OMe | CH | |
| 20 | Me | CO—Et | H | Na | Me | Me | CH | |
| 21 | Me | CO—Et | H | Na | OMe | OMe | N | |
| 22 | Me | CO—Et | H | Na | OMe | Me | N | |
| 23 | Me | CO—Et | H | K | OCH₂CF₃ | NMe₂ | N | |
| 24 | Me | CO—ⁱPr | H | Na | OMe | OMe | CH | 214–215 (dec.) |
| 25 | Me | CO—ⁱPr | H | K | OMe | OMe | CH | |
| 26 | Me | CO—ⁿPr | H | Na | OMe | OMe | CH | |
| 27 | Me | CO—ᶜPr | H | Na | OMe | OMe | CH | 217 (dec.) |
| 28 | Me | COOMe | H | Na | OMe | OMe | CH | 173 (dec.) |
| 29 | Me | COOMe | H | K | OMe | OMe | CH | |
| 30 | Me | COOMe | H | NMe₄ | OMe | OMe | CH | |
| 31 | Me | COOMe | H | NH₄ | OMe | OMe | CH | |
| 32 | Me | COOMe | H | Na | OMe | Me | CH | |
| 33 | Me | COOMe | H | Na | Cl | OMe | CH | |
| 34 | Me | COOMe | H | Na | Me | Me | CH | |
| 35 | Me | COOMe | H | Na | OMe | OMe | N | 198(dec.) |
| 36 | Me | COOMe | H | K | OMe | OMe | N | |
| 37 | Me | COOMe | H | Na | OMe | Me | N | 218–210 (dec.) |
| 38 | Me | COOMe | H | K | OMe | Me | N | |
| 39 | Me | COOMe | H | K | OCH₂CF₃ | NMe₂ | N | |
| 40 | Me | COOMe | Me | Na | OMe | OMe | CH | |
| 41 | Me | COOMe | Me | Na | OMe | Me | N | |
| 42 | Me | COOEt | H | Na | OMe | Me | N | |
| 43 | Me | COOEt | H | K | OMe | Me | N | |
| 44 | Me | COOEt | H | NHEt₃ | OMe | Me | N | |
| 45 | Me | COOEt | H | Na | OMe | OMe | N | |
| 46 | Me | COOEt | H | Na | OMe | OMe | CH | |
| 47 | Me | COOEt | H | Na | OMe | Me | CH | |
| 48 | Me | COOEt | H | Na | Me | Me | CH | |
| 49 | Me | COOEt | H | Na | Cl | OMe | CH | |
| 50 | Me | COOCH₂CH₂Cl | H | Na | OMe | OMe | CH | |
| 51 | Me | CO—NHEt | H | Ne | OMe | OMe | CH | |
| 52 | Me | SO₂Me | H | Na | OMe | OMe | CH | |
| 53 | Me | SO₂Me | H | Na | OMe | Me | N | |
| 54 | Me | SO₂Me | H | Na | OMe | Cl | CH | |
| 55 | Me | SO₂NHMe | H | Na | OMe | Cl | CH | |
| 56 | Me | SO₂NHMe | H | Na | OMe | OMe | CH | |
| 57 | Me | CHO | H | Na | OMe | OMe | CH | 202 (dec.) |
| 58 | Me | CHO | H | Na | Cl | OMe | CH | |
| 59 | Me | CHO | H | Na | Me | OMe | CH | |
| 60 | Me | CHO | H | Na | Me | Me | CH | |
| 61 | Me | CHO | H | Na | OMe | OMe | N | |
| 62 | Me | CHO | H | Na | OMe | Me | N | |
| 63 | Me | CHO | H | Na | NMe₂ | OCH₂CF₃ | N | |
| 64 | Me | CO—CF₃ | H | Na | OMe | OMe | CH | 212–215 (dec.) |
| 65 | Me | CO—CF₃ | H | Na | OMe | Cl | CH | |
| 66 | Me | CO—CF₃ | H | Na | OMe | Me | CH | |
| 67 | Me | CO—CF₃ | H | Na | OMe | OMe | N | |
| 68 | Me | CO—CF₃ | H | Na | OMe | Me | N | |

TABLE 1-continued $$R^2-HN-\text{benzene}(COOR^1)(SO_2-N^{\ominus}M^{\oplus}-CO-NR^3-\text{triazine}(Y,Z,X))$$

| No. | R¹ | R² | R³ | M | X | Y | Z | m.p. [°C.] |
|---|---|---|---|---|---|---|---|---|
| 69 | Et | CO—Me | H | Na | OMe | OMe | CH | |
| 70 | ⁿPr | CO—Me | H | Na | OMe | OMe | CH | |
| 71 | CH₂CH₂Cl | CO—Me | H | Na | OMe | OMe | CH | |
| 72 | Et | CO—H | H | Na | OMe | OMe | CH | |
| 73 | Et | COCF₃ | H | Na | OMe | OMe | CH | |
| 74 | ⁿPr | CO—H | H | Na | OMe | OMe | CH | |
| 75 | ⁿPr | CO—CF₃ | H | Na | OMe | OMe | CH | |
| 76 | oxetanyl | CO—CH₃ | H | Na | OMe | OMe | CH | |
| 77 | " | CO—H | H | Na | OMe | OMe | CH | |
| 78 | dimethyl-oxetanyl | CO—H | H | Na | OMe | OMe | CH | |
| 79 | CH₂-oxetanyl | CO—H | H | Na | OMe | OMe | CH | |
| 80 | " | CO—H | H | Na | OMe | OMe | CH | |
| 81 | —CH₂-oxiranyl | CO—H | H | Na | OMe | OMe | CH | |
| 82 | " | CO—CH₃ | H | Na | OMe | OMe | CH | |
| 83 | CH₂CH₂Cl | CO—H | H | Na | OMe | OMe | CH | |
| 84 | CH₂CH₂F | CO—H | H | Na | OMe | OMe | CH | |
| 85 | CH₂CH₂—OMe | CO—H | H | Na | OMe | OMe | CH | |
| 86 | CH₂CF₃ | CO—H | H | Na | OMe | OMe | CH | |

B. Formulation Examples a) A dust is obtained by mixing 10 parts by weight of a compound of the formula (I) and 90 parts by weight of talc as inert substance and comminuting the mixture in a hammer mill.

b) A wettable powder which is readily dispersible in water is obtained by mixing 25 parts by weight of a compound of the formula (I), 64 parts by weight of kaolin-containing quartz as inert substance, 10 parts by weight of potassium ligninsulfonate and 1 part by weight of sodium oleoylmethyltaurinate as wetting agent and dispersant, and grinding the mixture in a pinned-disk mill.

c) A dispersion concentrate which is readily dispersible in water is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example approximately 255° to above 277° C.) and grinding the mixture in a ball mill to a fineness of below 5 microns.

d) An emulsifiable concentrate is obtained from 15 parts by weight of a compound of the formula (I),
75 parts by weight of cyclohexanone as solvent and
10 parts by weight of oxethylated nonylphenol as emulsifier.

e) Water-dispersible granules are obtained by mixing 75 parts by weight of a compound of the formula (I),
10 parts by weight of calcium ligninsulfonate,
5 parts by weight of sodium lauryl sulfate,
3 parts by weight of polyvinyl alcohol and
7 parts by weight of kaolin, grinding the mixture on a pinned-disk mill and granulating the powder in a fluidized bed by spraying on water as granulation liquid.

f) Water-dispersible granules are also obtained by homogenizing and precomminuting, in a colloid mill, 25 parts by weight of a compound of the formula (I),
5 parts by weight of sodium 2,2'-dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water, subsequently grinding the mixture in a bead mill and atomizing and drying the resulting suspension in a spray tower by means of a single-substance nozzle.

C. Biological Examples

1. Pre-emergence activity against weeds

Seeds or rhizome pieces of monocotyledon and dicotyledon weed plants are placed in sandy loam soil in plastic pots and covered with soil. The compounds according to the invention, which are formulated as wettable powders or emulsion concentrates, are then applied to the surface of the soil cover in the form of aqueous suspensions or emulsions at an application rate of 600 to 800 l of water/ha (converted), in various dosages.

After the treatment, the pots are placed in a greenhouse and kept under good growth conditions for the weeds. After the test plants have emerged, the damage to the plants or the negative effect on the emergence was scored visually after a test period of 3 to 4 weeks had elapsed, by comparison with untreated controls. As shown by the test results, the compounds according to the invention have a good herbicidal pre-emergence activity against a wide range of grass weeds and broad-leaved weeds. For example, the compounds of Examples 1, 2, 17, 24, 27, 28, 35, 37, 57, 64, 72, 73, 74 and 75 of Table 1 have a very good herbicidal activity against harmful plants such as *Alopecurus myosuroides, Sinapis alba, Chrysanthemum segetum, Avena sativa, Stellaria media, Echinochloa crusgalli* and *Lolium multiflorum* when applied pre-emergence at an application rate of 0.3 kg and less of active ingredient per hectare.

2. Post-emergence activity against weeds

Seeds or rhizome pieces of mono- and dicotyledon weeds are placed in sandy loam soil in plastic pots, covered with soil and grown in a greenhouse under good growth conditions. Three weeks after sowing, the test plants are treated in the three-leaf stage.

The compounds according to the invention, which are formulated as wettable powders or emulsion concentrates, are sprayed in various dosages onto the green parts of the plants at an application rate of 600 to 800 l of water/ha (converted) and, after the test plants have remained in the greenhouse for about 3 to 4 weeks under optimum growth conditions, the activity of the preparations was scored visually in comparison with untreated controls. The compositions according to the invention also have a good herbicidal post-emergence activity against a wide range of economically important grass weeds and broad-leaved weeds. For example, the compounds of Examples 1, 2, 17, 24, 27, 28, 35, 37, 57, 64, 72, 73, 74 and 75 of Table 1 have a very good herbicidal activity against harmful plants such as *Alopecurus myosuroides, Sinapis alba, Stellaria media, Echinochloa crus-galli, Lolium multiflorum, Chrysanthemum segetum* and *Avena sativa* when applied post-emergence at an application rate of 0.3 kg or less of active ingredient per hectare.

3. Tolerance by crop plants

In further greenhouse experiments, seeds of a substantial number of crop plants and weeds are placed in sandy loam soil and covered with soil. Some of the pots are treated immediately as described under Section 1 while the remaining pots are placed in the greenhouse until the plants have developed two to three true leaves and then sprayed with various dosages of the substances of the formula (I) according to the invention, as described in Section 2. Visual scoring four to five weeks after the application and after the plants have remained in the greenhouse reveals that the compounds according to the invention do not inflict any damage to dicotyledon crops such as, for example, soya, cotton, oilseed rape, sugar beet and potatoes when used pre- and post-emergence, even when high dosages of active substance are used. Moreover, some substances also left Gramineae crops such as, for example, wheat, barley, rye, Sorghum species, maize or rice, unharmed. The compounds of the formula (I) therefore have a high selectivity when used for controlling undesirable vegetation in agricultural crops.

We claim:

1. A compound of the formula (I) (a salt),

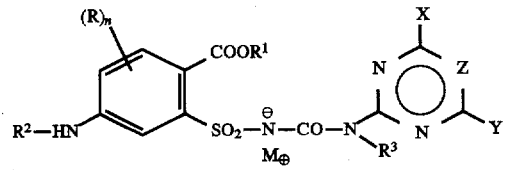

in which n 0, 1, 2 or 3,

R is halogen, $C_1-C_3$-alkyl or $C_1-C_3$-alkoxy, in each case independently of other substituents R in the event that n is greater than 1, $R^1$ is $C_1-C_6$-alkyl, $C_2-C_6$-alkenyl, $C_2-C_6$-alkinyl, $C_3-C_6$-cycloalkyl, each of the four last-mentioned radicals being unsubstituted or substituted by one or more radicals selected from the group consisting of halogen, CN, $C_1-C_4$-alkoxy, $C_1-C_4$-haloalkoxy, mono-($C_1-C_4$-alkyl)amino, di($C_1-C_4$-alkyl)-amino, $C_1-C_4$-alkylsulfonyl, $C_1-C_4$-alkylsulfinyl, ($C_1-C_4$-alkoxy)-carbonyl, aminocarbonyl, mono-($C_1-C_4$-alkyl)-aminocarbonyl, di($C_1-C_4$-alkyl)-aminocarbonyl, unsubstituted phenyl, substituted phenyl, which has the meaning defined below, and a heterocyclic radical having 3 to 6 ring atoms and 1 hetero ring atom selected from N, O and S, which heterocyclic radical is unsubstituted or substituted by one or more $C_1-C_4$-alkyl, or is a heterocyclic radical having 3 to 6 ring atoms and 1 hetero ring atom selected from N, O and S, which heterocyclic radical is unsubstituted or substituted by one or more $C_1-C_4$-alkyl, wherein substituted phenyl means phenyl substituted by one or more radicals selected from the group consisting of halogen, $C_1-C_4$-alkyl, $C_1-C_4$-haloalkyl $C_1-C_4$-alkoxy, $C_1-C_4$-haloalkoxy, $C_1-C_4$-alkylthio, hydroxy, amino, nitro, cyano, $C_1-C_4$-alkoxy-carbonyl, $C_1-C_4$-alkylcarbonyl, formyl, carbamoyl, mono- and di-($C_1-C_4$-alkyl)-aminocarbonyl, mono- and di-($C_1-C_4$-alkyl)-amino, $C_1-C_4$-alkylsulfinyl, $C_1-C_4$-haloalkylsulfinyl, $C_1-C_4$-alkylsulfonyl and $C_1-C_4$-haloalkylsulfonyl, $R^2$ is an acyl radical selected from CO—$R^4$, CO—$OR^5$, CO—$NR^6R^7$ or $SO_2$—$R^8$, $R^3$ is H or $C_1-C_5$-alkyl, $R^4$ is H, $C_1-C_6$-alkyl, $C_2-C_6$-alkenyl, $C_2-C_6$-alkinyl, $C_3-C_6$-cycloalkyl, each of the four last-mentioned radicals being unsubstituted or substituted by one or more radicals selected from the group consisting of halogen, CN, $C_1-C_4$-alkoxy, $C_1-C_4$-haloalkoxy, mono-($C_1-C_4$-alkyl)amino, di-($C_1-C_4$-alkyl)-amino, $C_1-C_4$-alkylsulfonyl, $C_1-C_4$-alkylsulfinyl, ($C_1-C_4$-alkoxy)-carbonyl, aminocarbonyl, mono-($C_1-C_4$-alkyl) aminocarbonyl, di-($C_1-C_4$-alkyl)-aminocarbonyl, unsubstituted phenyl and substituted phenyl, which has a meaning as defined above under $R^1$, or is unsubstituted phenyl or is substituted phenyl, which has a meaning as defined above under $R^1$, $R^5$ is a radical selected from the group of radicals defined for $R^4$, except hydrogen, $R^6$, $R^7$ independently of one another are H, $C_1-C_6$-alkyl, $C_2-C_6$-alkenyl, $C_2-C_6$-alkinyl, each of the 3 last-mentioned radicals being unsubstituted or substituted by one or more radicals selected from the group consisting of halogen, CN, $C_1$–$C_4$-alkoxy, $C_1$–$C_4$-haloalkoxy, mono-($C_1$–$C_4$-alkyl)-amino, di-($C_1$–$C_4$-alkyl)-amino, $C_1$–$C_4$-alkylsulfonyl, $C_1$–$C_4$-alkylsulfinyl, ($C_1$–$C_4$-alkoxy)carbonyl, aminocarbonyl, mono-($C_1$–$C_4$-alkyl)aminocarbonyl and di-($C_1$–$C_4$-alkyl)-aminocarbonyl, or $R^6$ and $R^7$ together with the nitrogen atom to which they are bound are a saturated heterocyclic ring of four to 8 ring atoms, which is unsubstituted or substituted by one or more ($C_1$–$C_4$-alkyl), $R^8$ is $C_1$–$C_5$-alkyl, $C_2$–$C_5$-alkenyl, each of the 3 last-mentioned radicals being unsubstituted or substituted by one or more radicals selected from the group consisting of halogen, $C_1$–$C_4$-alkoxy, $C_1$–$C_4$-haloalkoxy, mono-($C_1$–$C_4$-alkyl)-amino and di-($C_1$–$C_4$-alkyl) amino, M⊕ is a metal- or ammonium ion, X, Y independently of one another are halogen, $C_1$–$C_6$-alkyl, $C_1$–$C_6$-alkoxy, $C_1$–$C_6$-alkylthio, each of the last-mentioned 3 radicals being unsubstituted or substituted by one or more radicals from the group consisting of halogen, $C_1$–$C_4$-alkoxy and $C_1$–$C_4$-alkylthio, or is $C_3$–$C_6$-cycloalkyl, $C_2$–$C_6$-alkenyl, $C_2$–$C_6$-alkinyl, $C_3$–$C_6$-alkenyloxy, $C_3$–$C_6$alkinyloxy, mono- or di-($C_1$–$C_4$-alkyl)amino and Z is CH.

2. A compound of formula (I) as claimed in claim 1, wherein n is 0, 1 or 2,

R is halogen, $C_1$–$C_3$-alkyl or $C_1$–$C_3$-alkoxy, $R^1$ is $C_1$–$C_6$-alkyl, $C_2$–$C_6$-alkenyl, $C_2$–$C_6$-alkinyl, $C_3$–$C_6$-cycloalkyl, each of the four last-mentioned radicals being unsubstituted or substituted by one or more radicals selected from the group consisting of halogen, CN, $C_1$–$C_4$-alkoxy, $C_1$–$C_4$-haloalkoxy, mono-($C_1$–$C_4$-alkyl)amino, di-($C_1$–$C_4$-alkyl)-amino, $C_1$–$C_4$-alkylsulfonyl, $C_1$–$C_4$-alkylsulfinyl, ($C_1$–$C_4$-alkoxy)-carbonyl, aminocarbonyl, mono-($C_1$–$C_4$-alkyl)-aminocarbonyl, di-($C_1$–$C_4$-alkyl)-aminocarbonyl, unsubstituted phenyl, phenyl substituted by one or more radicals selected from the group consisting of halogen, $C_1$–$C_4$-alkyl, $C_1$–$C_4$-haloalkyl $C_1$–$C_4$-alkoxy, $C_1$–$C_4$haloalkoxy and nitro, and a heterocyclic radical having 3 to 6 ring atoms and 1 hetero ring atom selected from N, O and S, which heterocyclic radical is unsubstituted or substituted by one or more $C_1$–$C_4$-alkyl, or is a heterocyclic radical having 3 to 6 ring atoms and 1 hetero ring atom selected from N, O and S, which heterocyclic radical is unsubstituted or substituted by one or more $C_1$–$C_4$-alkyl, $R^2$ is an acyl radical selected from CO—$R^4$, CO—$OR^5$, CO—$NR^6R^7$ or $SO_2$—$R^8$, $R^3$ is H or $C_1$–$C_5$-alkyl, $R^4$ is H, $C_1$–$C_6$-alkyl, $C_2$–$C_6$-alkenyl, $C_2$–$C_6$-alkinyl, $C_3$–$C_6$-cycloalkyl, each of the four last-mentioned radicals being unsubstituted or substituted by one or more radicals selected from the group consisting of halogen, CN, $C_1$–$C_4$-alkoxy, $C_1$–$C_4$-haloalkoxy, mono-($C_1$–$C_4$-alkyl)amino, di-($C_1$–$C_4$-alkyl)-amino, $C_1$–$C_4$-alkylsulfonyl, $C_1$–$C_4$-alkylsulfinyl, ($C_1$–$C_4$-alkoxy)-carbonyl, aminocarbonyl, mono-($C_1$–$C_4$-alkyl) aminocarbonyl, di-($C_1$–$C_4$-alkyl)-aminocarbonyl, unsubstituted phenyl and phenyl substituted by one or more radicals selected from the group consisting of halogen, $C_1$–$C_4$-alkyl, $C_1$–$C_4$-haloalkyl $C_1$–$C_4$alkoxy, $C_1$–$C_4$-haloalkoxy and nitro, or is unsubstituted phenyl or is phenyl substituted by one or more radicals selected from the group consisting of halogen, $C_1$–$C_4$-alkyl, $C_1$–$C_4$-haloalkyl$C_1$–$C_4$-alkoxy, $C_1$–$C_4$-haloalkoxy and nitro, $R^5$ is a radical selected from the group of radicals defined for $R^4$, except hydrogen, $R^6$, $R^7$ independently of one another are H, $C_1$–$C_6$-alkyl, $C_2$–$C_6$-alkenyl, $C_2$–$C_6$-alkinyl, each of the 3 last-mentioned radicals being unsubstituted or substituted by one or more radicals selected from the group consisting of halogen, CN, $C_1$–$C_4$-alkoxy, $C_1$–$C_4$-haloalkoxy, mono($C_1$–$C_4$-alkyl)-amino, di-($C_1$–$C_4$-alkyl)amino, $C_1$–$C_4$-alkylsulfonyl, $C_1$–$C_4$-alkylsulfinyl, ($C_1$–$C_4$-alkoxy)-carbonyl, aminocarbonyl, mono-($C_1$–$C_4$-alkyl)aminocarbonyl and di-($C_1$–$C_4$-alkyl)-aminocarbonyl, or $R^6$ and $R^7$ together with the nitrogen atom to which they are bound are a saturated heterocyclic ring of four to 8 ring atoms, which is unsubstituted or substituted by one or more ($C_1$–$C_4$-alkyl), $R^8$ is $C_1$–$C_5$-alkyl, $C_2$–$C_5$-alkenyl, each of the 3 last-mentioned radicals being unsubstituted or substituted by one or more radicals selected from the group consisting of halogen, $C_1$–$C_4$-alkoxy, $C_1$–$C_4$-haloalkoxy, mono-($C_1$–$C_4$-alkyl)-amino and di-($C_1$–$C_4$-alkyl) amino, M⊕ is the cation equivalent of an alkali metal or alkaline earth metal, or is $NH_4^+$, $½Zn^{2+}$, $R^oNH_3^+$, $R^o_2NH_2^+$ oder $R^o_4N^+$, $R^o$ is $C_1$–$C_6$-alkyl or benzyl, X, Y independently of one another are halogen, $C_1$–$C_4$-alkyl, $C_4$–$C_4$-alkoxy, $C_1$–$C_4$-alkylthio, each of the 3 last-mentioned radicals being unsubstituted or substituted by one or more radicals selected from the group consisting of halogen, $C_1$–$C_4$-alkoxy and $C_1$–$C_4$-alkylthio, or is mono- or di($C_1$–$C_4$-alkyl)amino, $C_3$–$C_6$-cycloalkyl, $C_2$–$C_5$-alkenyl or $C_2$–$C_5$-alkinyloxy and Z is CH.

3. A compound of the formula (I) as claimed in claim 1, wherein $R^1$ is $C_3$–$C_6$-alkyl, $C_2$–$C_6$-alkenyl, $C_2$–$C_6$-alkynyl or $C_3$–$C_6$-cycloalkyl, each of the four last-mentioned radicals being unsubstituted or substituted by one or more radicals selected from the group consisting of F, Cl, Br, I, CN, $OCH_3$, $OCF_3$, $N(CH_3)_2$, $SO_2CH_3$, $CO_2CH_3$, $CO_2N(CH_3)_2$ and phenyl, or is a radical of the formulae $A_1$ to $A_7$

(A₁)

(A₂)

(A₃)

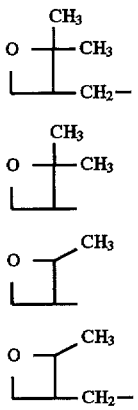

(A₄)
(A₅)
(A₆)
(A₇)

$R^2$ is CO—$R^4$, CO—$OR^5$, CO—$NR^6R^7$ or $SO_2$—$R^8$, $R^3$ is H or $CH_3$, $R^4$ is hydrogen, $C_1$–$C_6$-alkyl, $C_2$–$C_6$-alkenyl, $C_2$–$C_6$-alkynyl or $C_3$–$C_6$-cycloalkyl, each of the four last-mentioned radicals being unsubstituted or substituted by one or more radicals selected from the group consisting of F, Cl, Br, I, CN, $OCH_3$, $OCF_3$, $N(CH_3)_2$, $SO_2CH_3$, $CO_2CH_3$, $CON(CH_3)_2$ and phenyl, or is phenyl which is unsubstituted or up to trisubstituted by identical or different radicals selected from the group consisting of halogen, $CH_3$, $C_2H_5$, $OCH_3$, $OC_2H_5$, $CF_3$, $C_2H_5Cl$, $OCHF_3$ or $OCHF_2$, $R^5$ is analogous to $R^4$, with the exception of hydrogen, $R^6$ and $R^7$ independently of one another are H, $C_1$–$C_6$-alkyl, $C_2$–$C_6$-alkenyl or $C_2$–$C_6$-alkynyl, each of the three last-mentioned radicals being unsubstituted or substituted by one or more radicals selected from the group consisting of F, Cl, Br, CN, $OCH_3$, $OCF_3$, $N(CH_3)_2$, $SO_2CH_3$, $CO_2CH_3$ and $CON(CH_3)_2$, and $R^8$ is $C_1$–$C_5$-alkyl or $C_2$–$C_5$-alkenyl, each of the two last-mentioned radicals being unsubstituted or substituted by one or more radicals selected from the group consisting of F, Cl, Br, $OCH_3$ or $N(CH_3)_2$.

4. A compound of the formula (I) as claimed in claim 1, wherein $R^1$ is $C_1$–$C_6$-alkyl, $R^2$ is CO—$R^4$, CO—$OR^5$, CO—$NR^6R^7$ or $SO_2$—$R^8$, $R^3$ is H, $M^\oplus$ is $Na^+$, $K^+$, ½$Mg^{2+}$, ½$Ca^{2+}$, $NH_4^+$, $H_2NEt_2^+$, $H_3NC_4H_9^+$, $NH(C_2H_5)_3^+$, $N(C_2H_5)_4^+$, $N(CH_3)_4^+$, or $HN(CH_3)_3^+$, $R^\circ$ is $C_1$–$C_6$-alkyl, X and Y are $OCH_3$, $OC_2H_5$, $SCH_3$, $NHCH_3$, $N(CH_3)_2$, $CH_3$ or $OCH_2CF_3$.

5. A compound as claimed in claim 1, wherein n is zero, $R^1$ is $C_1$–$C_4$-alkyl, $R^2$ is formyl, ($C_1$–$C_4$-alkyl)-carbonyl, which is unsubstituted or substituted by one to three halogen atoms, or ($C_1$–$C_4$-alkoxy)-carbonyl, $R^3$ is hydrogen, $M^\oplus$ is an alkali metal or ammonium ion, X, Y independently of one another are $C_1$–$C_4$-alkoxy, which is unsubstituted or substituted by one or more halogen atoms, $C_1$–$C_4$-alkyl, dimethylamino or chloro.

6. A compound as claimed in claim 5, wherein $R^1$ is methyl, ethyl, n-propyl or i-propyl, $R^2$ is formyl, ($C_1$–$C_4$-alkyl)-carbonyl, $COCF_3$ or ($C_1$–$C_4$-alkoxy)-carbonyl, X, Y independently of one another are $OCH_3$, $OCHF_2$, $OCH_2CF_3$, $CH_3$, Cl or $N(CH_3)_2$.

7. A compound as claimed in claim 6, wherein $R^1$ is methyl, ethyl, n-propyl or i-propyl, $R^2$ is CHO, $CH_3CO$—, $C_2H_5CO$—, n—$C_3H_7CO$—, i—$C_3H_7CO$—, t—$C_4H_9CO$—, $CF_3CO$— or $CH_3O$—CO—, X, Y independently of one another are $OCH_3$, $OCHF_2$, $OCH_2CF_3$, $CH_3$, Cl or $N(CH_3)_2$.

8. A compound as claimed in claim 7, wherein $R^1$ is methyl, ethyl, n-propyl or i-propyl, $R^2$ is CHO, $CH_3CO$—, $C_2H_5CO$—, n—$C_3H_7CO$—, i—$C_3H_7CO$— or $CH_3O$—, CO—, $M^\oplus$ is $Na^+$, X is $OCH_3$ or $CH_3$ and Y is $OCH_3$, $CH_3$ or Cl.

9. A herbicidal or plant growth-regulating composition, which comprises at least one compound of the formula (I) as claimed in claim 1 and formulation auxiliaries conventionally used in crop protection.

10. A method of controlling harmful plants or of regulating the growth of plants, which comprises applying an effective amount of one or more of the compounds of the formula (I) as claimed in claim 11 to the harmful plants or plants, the seeds of these plants or the area on which the plants grow.

* * * * *